United States Patent
Kamo et al.

(10) Patent No.: US 11,903,560 B2
(45) Date of Patent: Feb. 20, 2024

(54) OBJECTIVE OPTICAL SYSTEM, IMAGE PICKUP APPARATUS, ENDOSCOPE AND ENDOSCOPE SYSTEM

(71) Applicant: OLYMPUS CORPORATION, Hachioji (JP)

(72) Inventors: Yuji Kamo, Hino (JP); Nobuhiko Sone, Hino (JP)

(73) Assignee: OLYMPUS CORPORATION, Tokyo (JP)

(*) Notice: Subject to any disclaimer, the term of this patent is extended or adjusted under 35 U.S.C. 154(b) by 790 days.

(21) Appl. No.: 17/028,347

(22) Filed: Sep. 22, 2020

(65) Prior Publication Data

US 2021/0096324 A1 Apr. 1, 2021

Related U.S. Application Data

(63) Continuation of application No. PCT/JP2018/030473, filed on Aug. 17, 2018.

(30) Foreign Application Priority Data

Mar. 27, 2018 (JP) ................................ 2018-059887

(51) Int. Cl.
*A61B 1/00* (2006.01)
*G02B 9/12* (2006.01)
(Continued)

(52) U.S. Cl.
CPC ............ *A61B 1/00188* (2013.01); *G02B 9/12* (2013.01); *G02B 23/243* (2013.01); *A61B 1/04* (2013.01)

(58) Field of Classification Search
CPC ........ A61B 1/00188; A61B 1/04; G02B 9/12; G02B 23/243
(Continued)

(56) References Cited

U.S. PATENT DOCUMENTS

| 7,466,490 B2 | 12/2008 | Igarashi |
| 9,297,985 B2 | 3/2016 | Sugita |
| 9,459,443 B2 | 10/2016 | Uzawa et al. |
| 9,739,997 B2 | 8/2017 | Takada |
| 9,766,437 B2 | 9/2017 | Sato |

(Continued)

FOREIGN PATENT DOCUMENTS

| JP | 2007094174 A | 4/2007 |
| JP | 2008107391 A | 5/2008 |

(Continued)

OTHER PUBLICATIONS

Bentley & Olson; Field Guide to Lens Design; Society of Photo-Optical Instrumentation Engineers (SPIE); p. 49; 2012 (Year: 2012).*

(Continued)

*Primary Examiner* — Mohammed A Hasan
(74) *Attorney, Agent, or Firm* — Holtz, Holtz & Volek PC

(57) ABSTRACT

An objective optical system includes, in order from an object side: a first group having a negative refractive power; a second group having a positive refractive power; and a third group having a positive refractive power, in which the first group and the third group are fixed and the second group is movable, the first group includes at least two lenses having a negative refractive power, the third group includes, in order from the object side, a 3-1st group having a positive refractive power, a 3-2nd group having a negative refractive power, a 3-3rd group having a positive refractive power, and a 3-4th group having a positive refractive power, and the following conditional expression (1)''' is satisfied:

$1.5 \leq Bk/f3 \leq 6$          (1)'''.

11 Claims, 9 Drawing Sheets

(51) Int. Cl.
*G02B 23/24* (2006.01)
*A61B 1/04* (2006.01)
(58) Field of Classification Search
USPC ....................................................... 359/784
See application file for complete search history.

(56) References Cited

U.S. PATENT DOCUMENTS

| | | |
|---|---|---|
| 9,949,622 B2 | 4/2018 | Katakura |
| 2008/0180809 A1 | 7/2008 | Igarashi |
| 2014/0002908 A1 | 1/2014 | Sugita |
| 2014/0198231 A1* | 7/2014 | Itoh .................. H04N 25/615 348/222.1 |
| 2015/0042773 A1 | 2/2015 | Uzawa et al. |
| 2015/0268460 A1 | 9/2015 | Takada |
| 2017/0038563 A1 | 2/2017 | Sato |
| 2017/0049306 A1 | 2/2017 | Katakura |
| 2019/0064501 A1 | 2/2019 | Katakura |

FOREIGN PATENT DOCUMENTS

| | | | |
|---|---|---|---|
| JP | 2014010286 A | 1/2014 | |
| JP | 5607278 B1 | 10/2014 | |
| JP | 2016038547 A * | 3/2016 | ............. G02B 13/04 |
| JP | 2016038547 A | 3/2016 | |
| JP | 2016184136 A | 10/2016 | |
| JP | 2017209154 A | 11/2017 | |
| JP | 2017219783 A | 12/2017 | |
| WO | 2014088104 A1 | 6/2014 | |
| WO | 2016067838 A1 | 5/2016 | |
| WO | 2016132639 A1 | 8/2016 | |
| WO | 2017073292 A1 | 5/2017 | |
| WO | 2018008460 A1 | 1/2018 | |
| WO | WO-2018008460 A1 * | 1/2018 | ......... A61B 1/00096 |

OTHER PUBLICATIONS

International Preliminary Report on Patentability (IPRP) (and English language translation thereof) dated Oct. 8, 2020 issued in International Application No. PCT/JP2018/030473.
International Search Report (ISR) (and English translation thereof) dated Nov. 20, 2018 issued in International Application No. PCT/JP2018/030473.
Written Opinion dated Nov. 20, 2018 issued in International Application No. PCT/JP2018/030473.

* cited by examiner

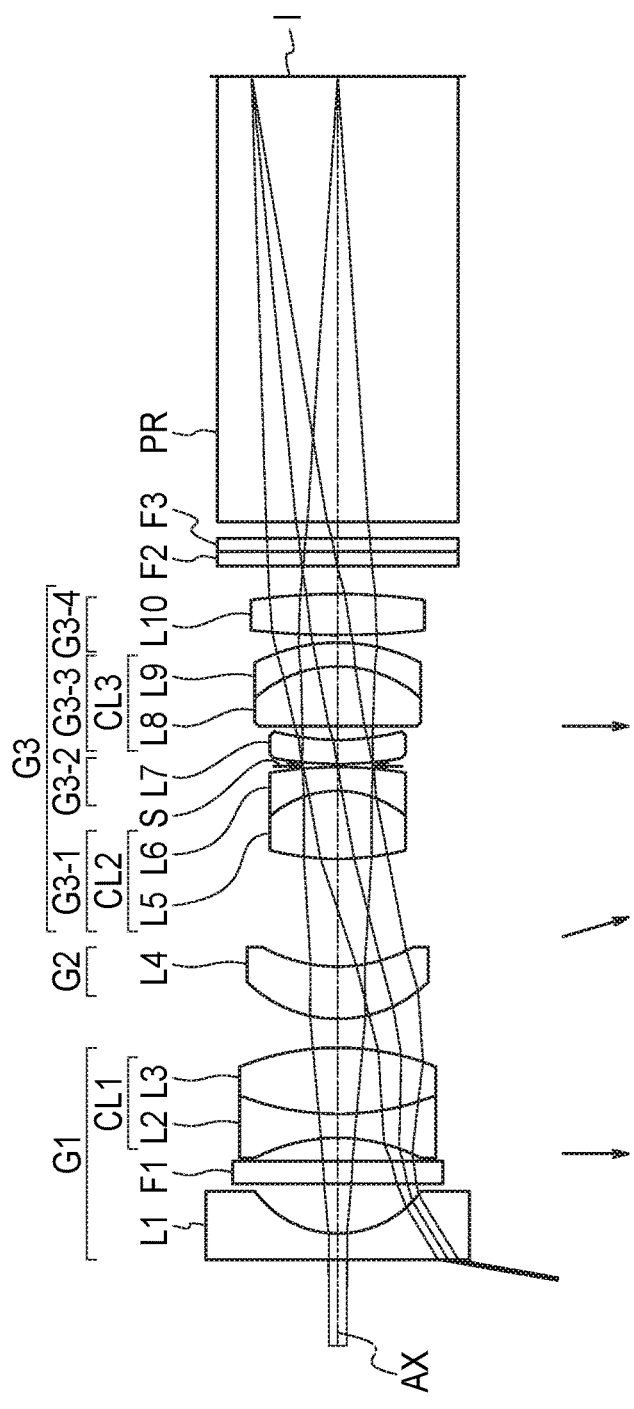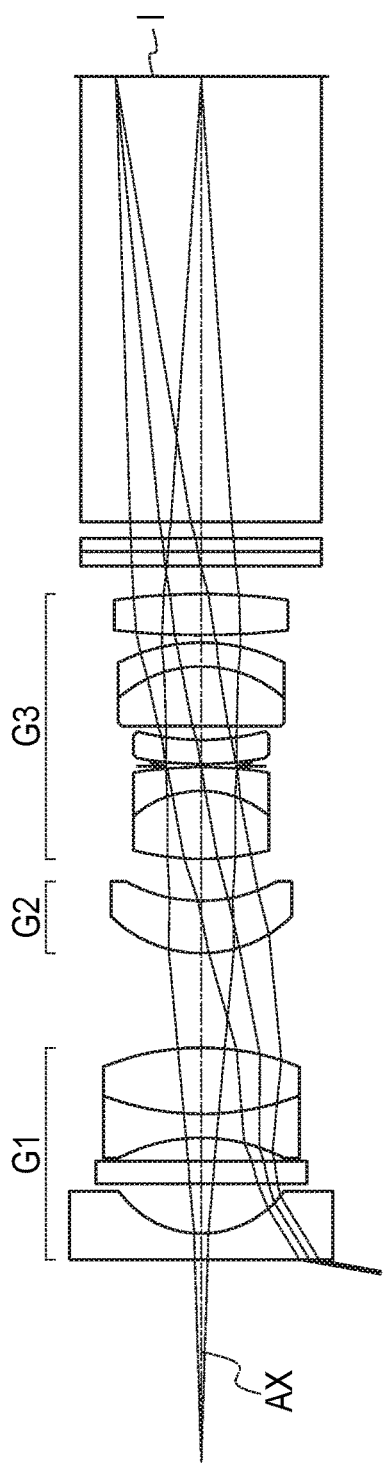
FIG. 1A
FIG. 1B

SA
FNO 4.416

-0.05  0.05
(mm)

AS
FIY 1.00

ΔM  ΔS

-0.05  0.05
(mm)

DT
FIY 1.00

-50.00  50.00
(%)

CC
FIY 1.00

-0.005  0.005
(mm)

SA
FNO 4.268

F LINE
d LINE
g LINE
C LINE

-0.05  0.05
(mm)

AS
FIY 1.00

-0.05  0.05
(mm)

DT
FIY 1.00

-50.00  50.00
(%)

CC
FIY 1.00

-0.005  0.005
(mm)

435.83 – – –
486.13 –·–·–
656.27 ·······
587.56 ———

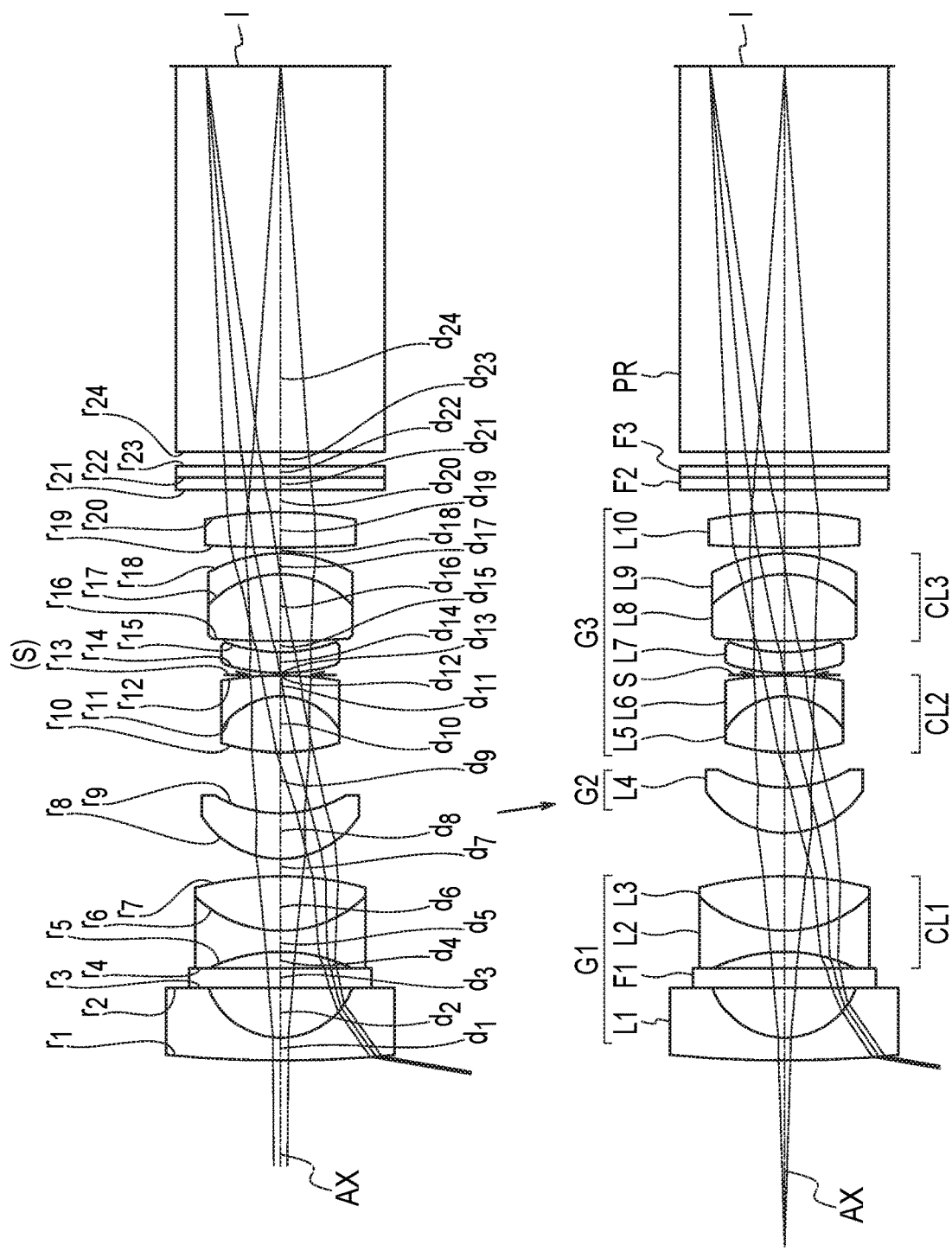

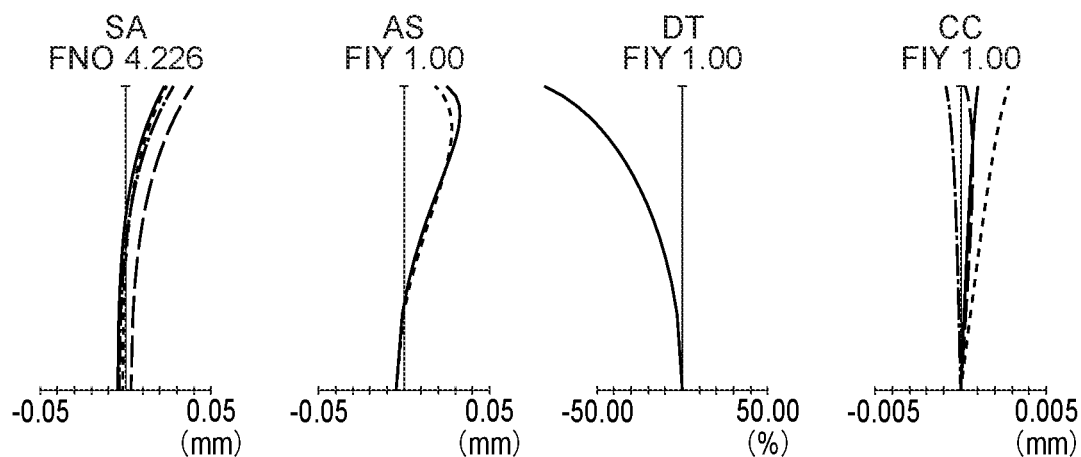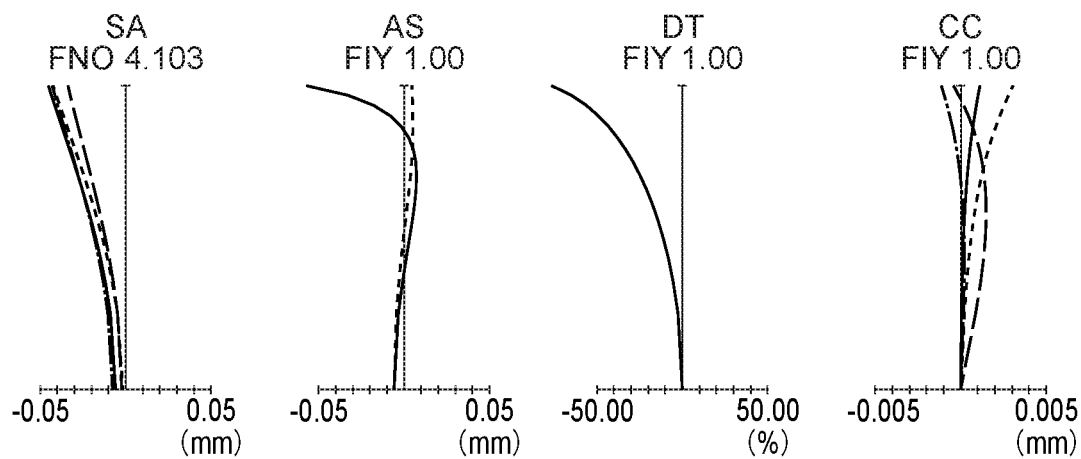

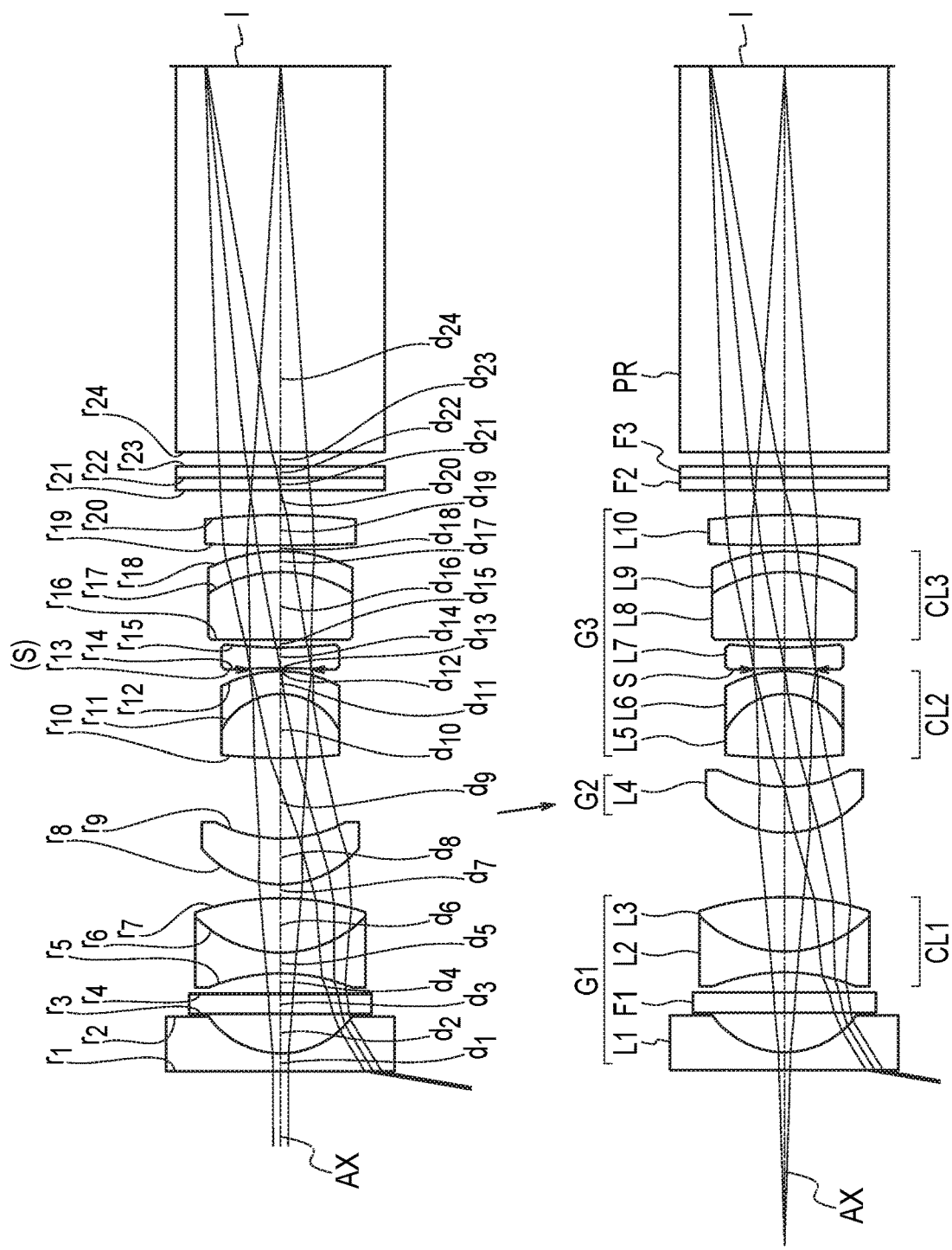

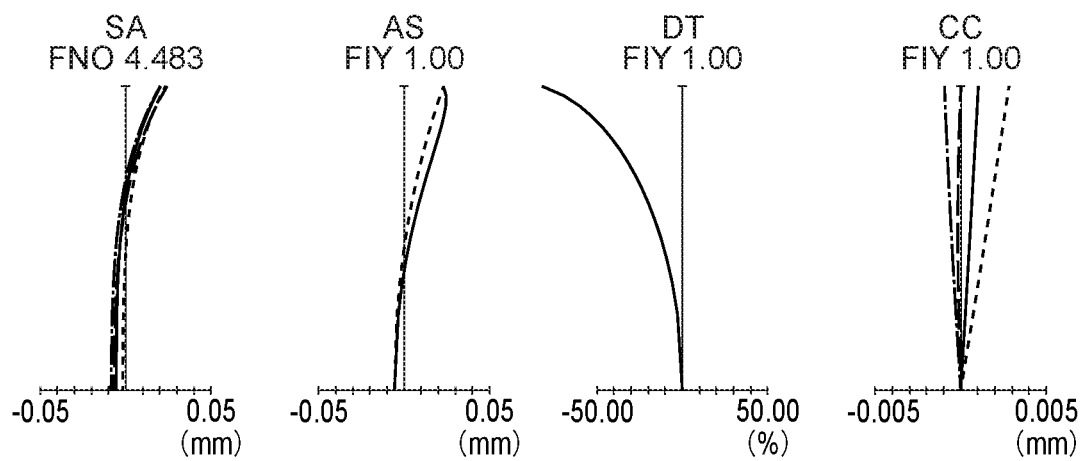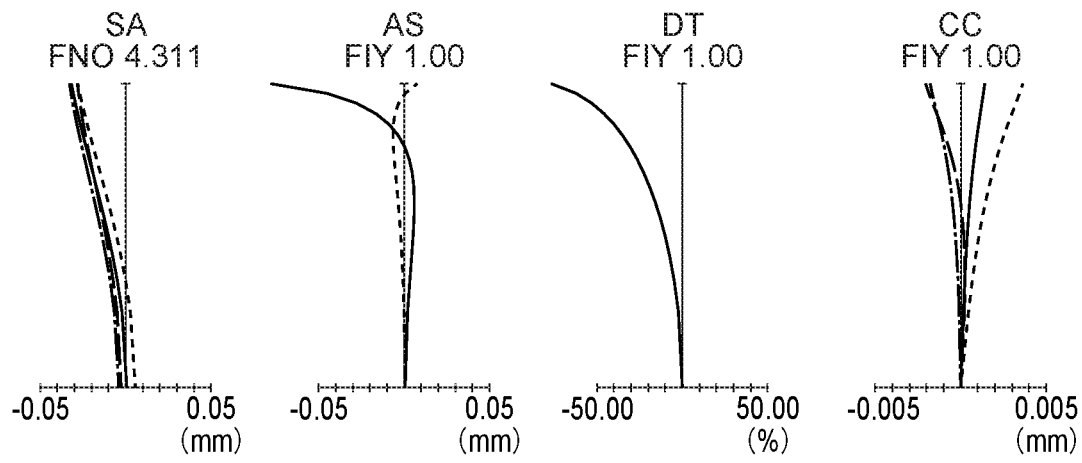

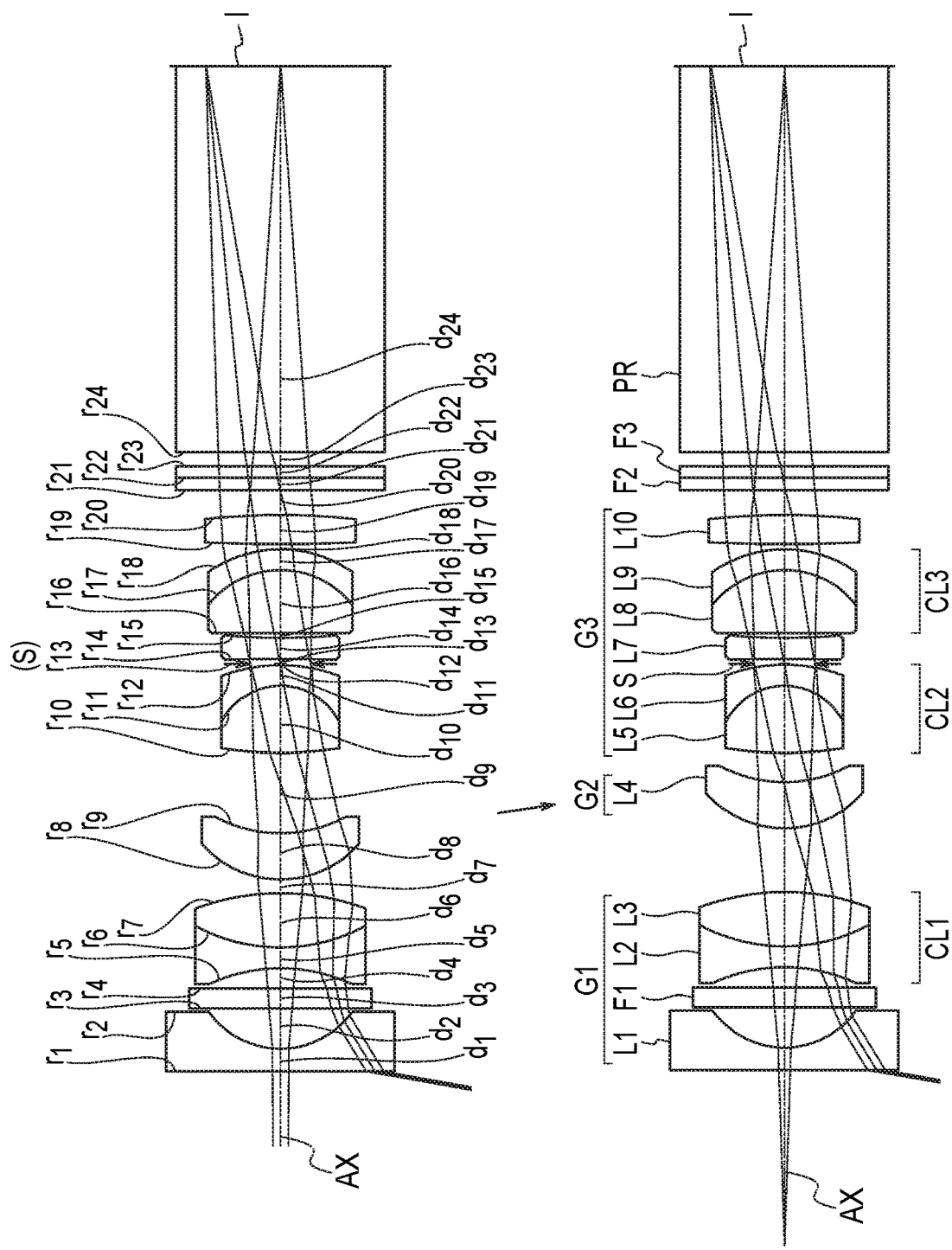

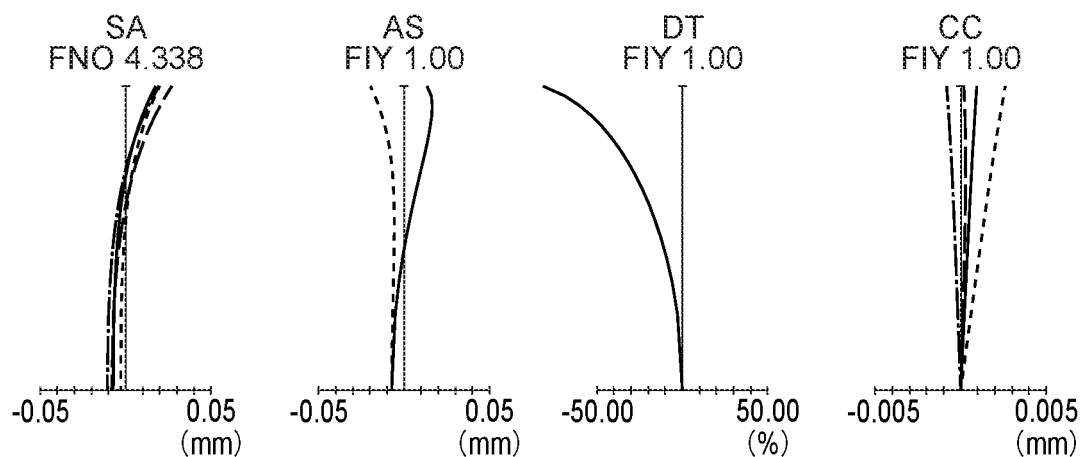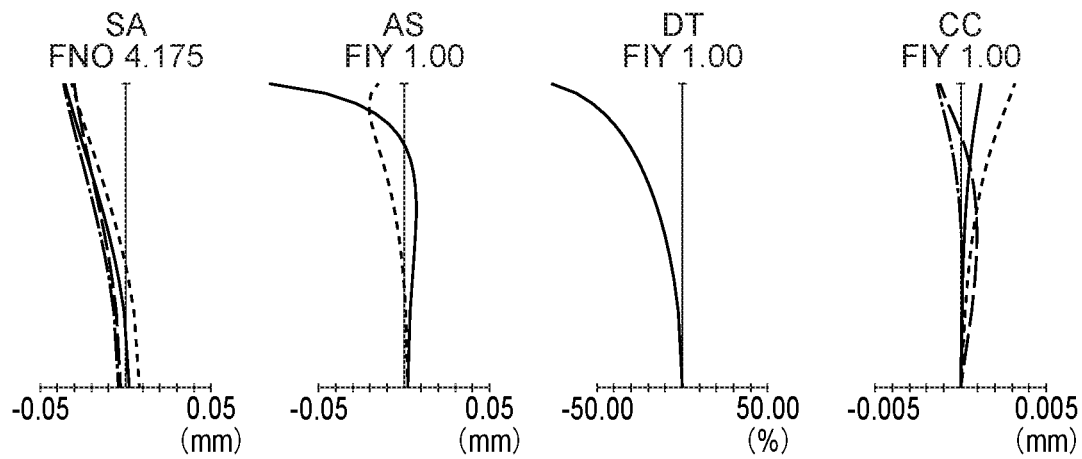

OBJECTIVE OPTICAL SYSTEM, IMAGE PICKUP APPARATUS, ENDOSCOPE AND ENDOSCOPE SYSTEM

CROSS-REFERENCE TO RELATED APPLICATION

The present application is a continuation of PCT/JP2018/030473, filed on Aug. 17, 2018 which is based upon and claims the benefit of priority from Japanese Patent Application Nos. 2018-059887 filed on Mar. 27, 2018; the entire contents of which are incorporated herein by reference.

BACKGROUND

Technical Field

The present disclosure relates to an objective optical system, an image pickup apparatus, an endoscope, and an endoscope system. The present disclosure particularly relates to an objective optical system with a long back focus. An objective optical system with a long back focus is suitable for an objective optical system, an image pickup apparatus, an endoscope, and an endoscope system used in, for example, the medical field and the industrial field.

Description of the Related Art

An endoscope is an apparatus widely used in the medical field and the industrial field. In particular, in the medical field, an endoscope is inserted into a body cavity to obtain a picture in the body cavity. Endoscopes for the medical field are used for examining and curing an observed site.

A conventional objective optical system has obtained pictures in an in-focus state within a range from a near point to a far point by setting a favorable Fno (F-number) and a favorable in-focus point. As the pixels of an image sensor has increased, however, a depth of field has developed a tendency to be narrow. Under the circumstance, there is a configuration having a focusing function for changing an in-focus position by moving some lenses of an optical system. For example, Japanese Patent Application Publication No. 2008-107391 and Japanese Patent Application Publication No. 2017-219783 each propose an objective optical system having a focusing function.

In addition, another objective optical system with a different configuration has been proposed to expand a depth of field. In this optical system, a polarizing prism disposed on an optical path divides the optical path into two optical paths. An image sensor obtains a far point picture and a near point picture developed by two light fluxes thus split at once. Then, a picture in an in-focus state is synthesized on the basis of the far point picture and the near point picture using image processing. Accordingly, it is possible to expand the depth of field of the objective optical system. An objective optical system having a polarizing prism needs a quite long back focus. For example, Japanese Patent No. 5607278 and WO2016/067838 each propose an optical system with a long back focus having a polarizing prism disposed therein.

SUMMARY

In a first aspect, an objective optical system according to the present disclosure includes, in order from an object side:
a first group having a negative refractive power;
a second group having a positive refractive power; and
a third group having a positive refractive power, wherein the first group and the third group are fixed and the second group is movable,
the first group includes at least two lenses having a negative refractive power,
the third group includes, in order from the object side, a 3-1st group having a positive refractive power, a 3-2nd group having a negative refractive power, a 3-3rd group having a positive refractive power, and a 3-4th group having a positive refractive power, and
the following conditional expression (1)''' is satisfied:

$$1.5 \leq Bk/f3 \leq 6 \tag{1'''}$$

where
Bk denotes a distance from a surface of the third group positioned nearest to an image to an image plane along an optical axis, and
f3 denotes a focal length of the third group.

In another aspect, an image pickup apparatus according to the present disclosure includes the aforementioned objective optical system.

In still another aspect, an endoscope according to the present disclosure includes the aforementioned objective optical system.

In yet another aspect, an endoscope system according to the present disclosure includes: the aforementioned endoscope; and an image processor.

BRIEF DESCRIPTION OF THE DRAWINGS

FIG. 1A is a sectional view of a lens of an objective optical system for an endoscope in a normal observation state according to an embodiment. FIG. 1B is a sectional view of the lens of the objective optical system for an endoscope in a close observation state according to the embodiment;

FIG. 4A is a sectional view of a lens of an objective optical system for an endoscope in the normal observation state according to Example 2. FIG. 4B is a sectional view of the lens of the objective optical system for an endoscope in the close observation state according to Example 2;

FIG. 5A illustrates spherical aberration (SA) in the normal observation state, FIG. 5B illustrates astigmatism (AS) in the normal observation state, FIG. 5C illustrates distortion (DT) in the normal observation state, and FIG. 5D illustrates a chromatic aberration of magnification (CC) in the normal observation state, for the objective optical system for an endoscope according to Example 2. FIG. 5E illustrates spherical aberration (SA) in the close observation state, FIG.

5F illustrates astigmatism (AS) in the close observation state, FIG. 5G illustrates distortion (DT) in the close observation state, and FIG. 5H illustrates a chromatic aberration of magnification (CC) in the close observation state, for the objective optical system for an endoscope according to Example 2;

FIG. 6A is a sectional view of a lens of an objective optical system for an endoscope in the normal observation state according to Example 3. FIG. 6B is a sectional view of the lens of the objective optical system for an endoscope in the close observation state according to Example 3;

FIG. 7A illustrates spherical aberration (SA) in the normal observation state, FIG. 7B illustrates astigmatism (AS) in the normal observation state, FIG. 7C illustrates distortion (DT) in the normal observation state, and FIG. 7D illustrates a chromatic aberration of magnification (CC) in the normal observation state, for the objective optical system for an endoscope according to Example 3. FIG. 7E illustrates spherical aberration (SA) in the close observation state, FIG. 7F illustrates astigmatism (AS) in the close observation state, FIG. 7G illustrates distortion (DT) in the close observation state, and FIG. 7H illustrates a chromatic aberration of magnification (CC) in the close observation state, for the objective optical system for an endoscope according to Example 3;

FIG. 8A is a sectional view of a lens of an objective optical system for an endoscope in the normal observation state according to Example 4. FIG. 8B is a sectional view of the lens of the objective optical system for an endoscope in the close observation state according to Example 4; and FIG. 9A illustrates spherical aberration (SA) in the normal observation state, FIG. 9B illustrates astigmatism (AS) in the normal observation state, FIG. 9C illustrates distortion (DT) in the normal observation state, and FIG. 9D illustrates a chromatic aberration of magnification (CC) in the normal observation state, for the objective optical system for an endoscope according to Example 4. FIG. 9E illustrates spherical aberration (SA) in the close observation state, FIG. 9F illustrates astigmatism (AS) in the close observation state, FIG. 9G illustrates distortion (DT) in the close observation state, and FIG. 9H illustrates a chromatic aberration of magnification (CC) in the close observation state, for the objective optical system for an endoscope according to Example 4.

DETAILED DESCRIPTION

Figures 2A, 2B:
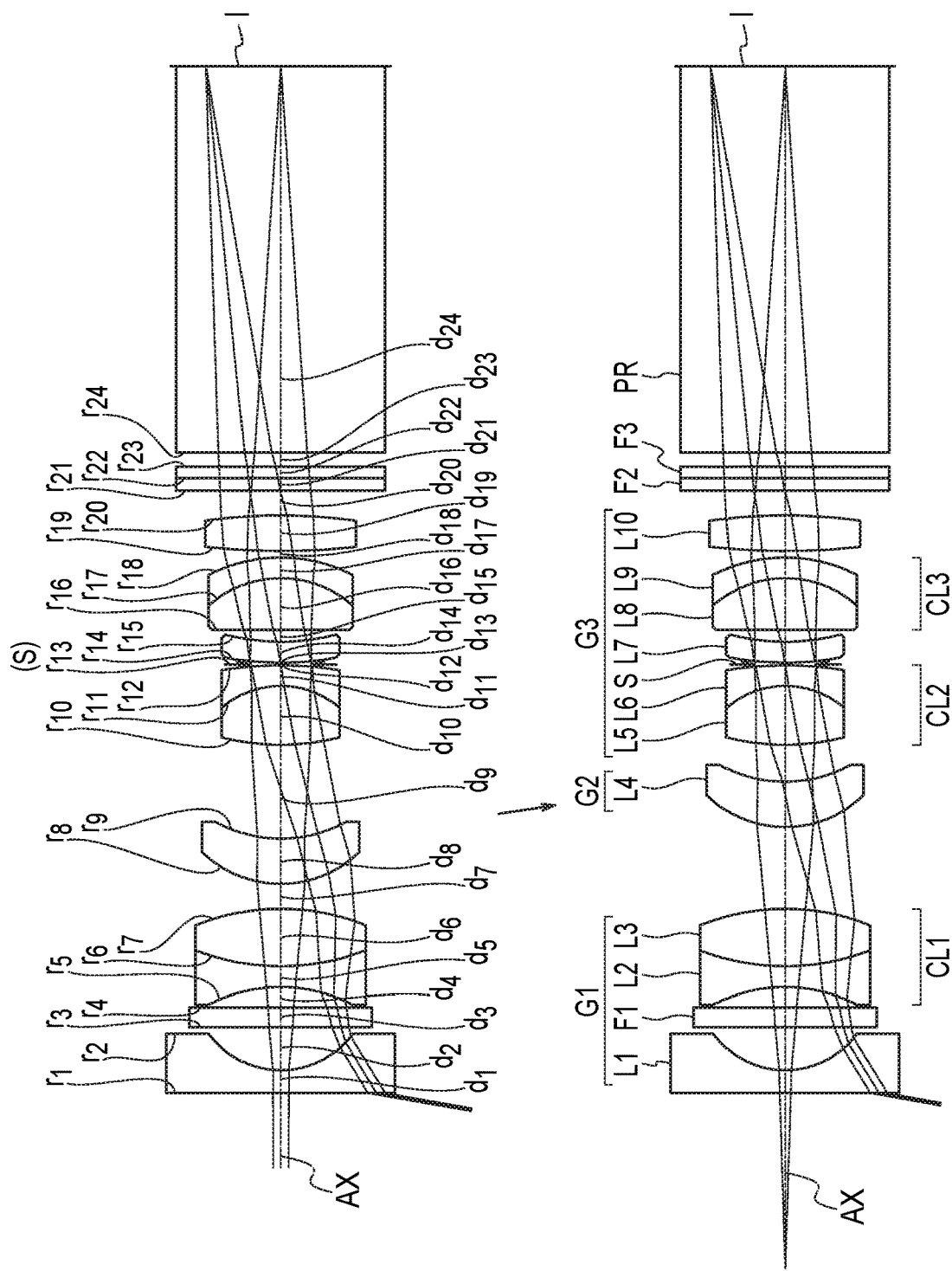
FIG. 2A is a sectional view of a lens of an objective optical system for an endoscope in the normal observation state according to Example 1.
FIG. 2B is a sectional view of the lens of the objective optical system for an endoscope in the close observation state according to Example 1.

An embodiment of an objective optical system, an image pickup apparatus, an endoscope, and an endoscope system according to the present disclosure will be explained hereinafter in detail on the basis of the drawings. The present disclosure is not limited to the following embodiment.

The explanation is made using an objective optical system for an endoscope as an example of the objective optical system.

Embodiment

FIG. 1A is a sectional view of a lens of an objective optical system for an endoscope in a normal observation state according to an embodiment. FIG. 1B is a sectional view of the lens of the objective optical system for an endoscope in a close observation state according to the embodiment. A second group G2 moves toward an image side when changing from a normal observation state to a close observation state.

The objective optical system for an endoscope according to the present embodiment includes, in order from an object side: a first group G1 having a negative refractive power; a second group G2 having a positive refractive power; and a third group G3 having a positive refractive power. The first group G1 and the third group G3 are fixed and the second group G2 is movable. The first group G1 includes at least two lenses having a negative refractive power, and the third group G3 includes, in order from the object side, a 3-1st group G3-1 having a positive refractive power, a 3-2nd group G3-2 having a negative refractive power, a 3-3rd group G3-3 having a positive refractive power, and a 3-4th group G3-4 having a positive refractive power.

The reasons for adopting the aforementioned configuration and the effects thereof in the present embodiment will be explained hereinafter. A retrofocus design in which a negative group and a positive group are basically arranged in this order from an object is adopted to secure a long back focus. In addition, a positive focusing group is disposed between the negative group and the positive group. By moving the positive focusing group, focusing is performed. That is, the first group G1 having a negative refractive power, the second group G2 having a positive refractive power, and the third group G3 having a positive refractive power are arranged in this order from an object in the present embodiment.

In order to obtain a long back focus in such a design, both the refractive power of the first group G1 having a negative refractive power and the refractive power of the third group G3 having a positive refractive power need to be large. In an endoscope, however, lenses need to have small diameters. For this reason, if an aperture stop S is disposed between the first group G1 having a negative refractive power and the third group G3 having a positive refractive power to reduce a ray height, configurations of refractive powers on both sides of the aperture stop S may have considerably asymmetric balance. Such a design makes it difficult to correct aberrations.

For this reason, in the first group G1 having a negative refractive power, at least two negative lenses are disposed, and thereby a large refractive power is distributed and generation of aberrations is suppressed.

As described above, however, there is a limit on correction of aberrations by the first group G1 having a negative refractive power, and therefore, the present embodiment focuses on the third group G3 and aims at improving an aberration correcting performance of the third group G3. For this reason, the 3-1st group G3-1 having a positive refractive power is disposed on the side of the third group G3 positioned nearest to the object, whereby light rays are converged and the ray height is reduced, and the 3-2nd group G3-2 having a negative refractive power is disposed on the image side of the third group G3, so that the aberrations generated in the positive group are corrected. Thus, the positive refractive power contributing to imaging is distributed to the 3-3rd group G3-3 and the 3-4th group G3-4, and therefore, the amount of generated aberrations can be reduced even if the refractive power becomes large.

With this configuration, it is possible to, in the present embodiment, favorably correct longitudinal chromatic aberration and chromatic aberration of magnification while securing a large refractive power, and also to suppress the generation of astigmatism and coma.

In addition, by disposing the aperture stop S between the 3-1st group G3-1 and the 3-2nd group G3-2, it is possible to decrease the ray height in the third group G3, thereby reducing the size of the lens. It is possible to favorably correct Chromatic aberration of magnification and astigmatism, in particular.

According to a preferred aspect of the present embodiment, it is preferable that the following conditional expression (1) be satisfied. The conditional expression (1) defines an appropriate ratio of Bk to f3. The refractive powers of the first group G1 and the third group G3 need to be large to secure a back focus. The conditional expression (1) considers the balance to the aberrations remaining in the first group G1.

$$1 \leq Bk/f3 \leq 6 \qquad (1)$$

where

Bk denotes a distance from a surface of the third group G3 positioned nearest to an image to an image plane along an optical axis, and f3 denotes a focal length of the third group G3.

When the conditional expression (1) takes a value larger than the upper limit value thereof, the refractive power of the third group G3 becomes excessively large whereby aberration is undercorrected, and as a result, the performance degrades.

When the conditional expression (1) takes a value smaller than the lower limit value thereof, the back focus becomes excessively short, and thus a polarizing prism cannot be disposed therein.

It is more preferable that the following conditional expression (1)' be satisfied:

$$1.2 \leq Bk/f3 \leq 5 \qquad (1)'$$

It is further preferable that the following conditional expression (1)" be satisfied:

$$1.5 \leq Bk/f3 \leq 4 \qquad (1)"$$

According to a preferred aspect of the present embodiment, it is preferable that the following conditional expression (2) be satisfied. The conditional expression (2) defines an appropriate ratio of f31 to f3. The 3-1st group G3-1 is disposed on the side of the third group G3 positioned nearest to the object. For this reason, it is desirable that generation of aberration be suppressed by the 3-1st group G3-1 to the utmost. The 3-1st group G3-1 is preferred to include a cemented lens CL2.

$$1.2 \leq f31/f3 \leq 5 \qquad (2)$$

where f31 denotes a focal length of the 3-1st group G3-1, and
f3 denotes the focal length of the third group G3.

When the conditional expression (2) takes a value larger than the upper limit value thereof, the refractive power of the 3-1st group G3-1 becomes excessively small and thus longitudinal chromatic aberration and spherical aberration are undercorrected.

When the conditional expression (2) takes a value smaller than the lower limit value thereof, the refractive power of the 3-1st group G3-1 becomes excessively large and thus longitudinal chromatic aberration and spherical aberration are overcorrected, and as a result, the optical performance degrades.

It is more preferable that the following conditional expression (2)' be satisfied:

$$1.35 \leq f31/f3 \leq 5 \qquad (2)'$$

It is further preferable that the following conditional expression (2)" be satisfied:

$$1.5 \leq f31/f3 \leq 4 \qquad (2)"$$

According to a preferred aspect of the present embodiment, it is preferable that the 3-3rd group G3-3 include a cemented lens and the following conditional expression (3) be satisfied. The conditional expression (3) defines appropriate ranges of f33 and f3. The 3-3rd group G3-3 has a positive refractive power related to imaging. For this reason, it is particularly preferred to reduce the generation of chromatic aberration. Accordingly, it is preferable that the 3-3rd group G3-3 include a cemented lens CL3.

$$1 \leq f33/f3 \leq 5 \qquad (3)$$

where f33 denotes a focal length of the 3-3rd group G3-3, and
f3 denotes the focal length of the third group G3.

When the conditional expression (3) takes a value larger than the upper limit value thereof, the refractive power of the 3-3rd group G3-3 becomes excessively small, and as a result, the total length becomes long and chromatic aberration is undercorrected.

When the conditional expression (3) takes a value smaller than the lower limit value thereof, the refractive power becomes excessively large, and as a result, spherical aberration and coma are undercorrected and chromatic aberration is overcorrected.

It is more preferable that the following conditional expression (3)' be satisfied:

$$1.2 \leq f33/f3 \leq 4 \qquad (3)'$$

It is further preferable that the following conditional expression (3)" be satisfied:

$$1.5 \leq f33/f3 \leq 3 \qquad (3)"$$

According to a preferred aspect of the present embodiment, it is preferable that the following conditional expression (4) be satisfied. The conditional expression (4) defines an appropriate ratio of f32 to f334. The 3-2nd group G3-2 having a negative refractive power is only the negative refractive power in the third group G3. For this reason, it is preferable that the 3-2nd group G3-2 be appropriately configured with respect to the 3-3rd group G3-3 and the 3-4th group G3-4 having a large refractive power related to imaging.

$$-30 \leq f32/f334 \leq -1.5 \qquad (4)$$

where f334 denotes a combined focal length of the 3-3rd group G3-3 and the 3-4th group G3-4, and
f32 denotes a focal length of the 3-2nd group G3-2.

When the conditional expression (4) takes a value larger than the upper limit value thereof, the negative refractive power of the 3-2nd group G3-2 becomes excessively small and thus spherical aberration, coma, and chromatic aberration are undercorrected, or, the positive refractive power of the 3-3rd group G3-3 and the 3-4th group G3-4 becomes excessively large and thus spherical aberration, and coma are under corrected.

When the conditional expression (4) takes a value smaller than the lower limit value thereof, the negative refractive power of the 3-2nd group G3-2 becomes excessively large and thus spherical aberration, coma, and chromatic aberration are overcorrected, or, the positive refractive power of the 3-3rd group G3-3 and the 3-4th group G3-4 becomes excessively small and thus the total length becomes long.

It is more preferable that the following conditional expression (4)' be satisfied:

$$-20 \leq f32/f334 \leq -2 \qquad (4)$$

It is further preferable that the following conditional expression (4)" be satisfied:

$$-15 \leq f32/f334 \leq -2.5 \quad (4)''$$

According to a preferred aspect of the present embodiment, it is preferable that the following conditional expression (5) be satisfied. The conditional expression (5) defines an appropriate ratio of f31 to f33. If the 3-1st group G3-1 and the 3-3rd group G3-3 with a negative refractive power interposed therebetween have an appropriately configured refractive power, it is possible to effectively correct aberration.

$$0.5 \leq f31/f33 \leq 5 \quad (5)$$

where f31 denotes a focal length of the 3-1st group G3-1, and
f33 denotes a focal length of the 3-3rd group G3-3.

When the conditional expression (5) takes a value larger than the upper limit value thereof, the relative refractive power of the 3-3rd group G3-3 becomes excessively large.

When the conditional expression (5) takes a value smaller than the lower limit value thereof, the relative refractive power of the 3-1st group G3-1 becomes excessively large and aberrations are undercorrected with the negative refractive power of the 3-2nd group G3-2, and as a result, spherical aberration, coma, and astigmatism deteriorate.

It is more preferable that the following conditional expression (5)' be satisfied:

$$0.6 \leq f31/f33 \leq 3.5 \quad (5)'$$

It is further preferable that the following conditional expression (5)" be satisfied:

$$0.7 \leq f31/f33 \leq 2.5 \quad (5)''$$

According to a preferred aspect of the present embodiment, it is preferable that the following conditional expression (6) be satisfied. The conditional expression (6) defines an appropriate ratio of f33 to f34. It is preferable that the 3-3rd group G3-3 and the 3-4th group G3-4 each having a positive refractive power mainly related to imaging have appropriately balanced refractive powers.

$$0.3 \leq f33/f34 \leq 2.5 \quad (6)$$

where f33 denotes a focal length of the 3-3rd group G3-3, and
f34 denotes a focal length of the 3-4th group G3-4.

When the conditional expression (6) takes a value larger than the upper limit value thereof, the refractive power of the 3-3rd group G3-3 becomes large and spherical aberration and thus longitudinal chromatic aberration deteriorate, or, the refractive power of the 3-4th group G3-4 becomes small and thus astigmatism deteriorates at the peripheral of the screen.

When the conditional expression (6) takes a value smaller than the lower limit value thereof, the refractive power of the 3-3rd group G3-3 becomes small and thus the total length becomes long, or, the relative refractive power of the 3-4th group G3-4 becomes large and thus astigmatism and chromatic aberration of magnification deteriorate.

It is more preferable that the following conditional expression (6)' be satisfied:

$$0.4 \leq f33/f34 \leq 2 \quad (6)'$$

It is further preferable that the following conditional expression (6)" be satisfied:

$$0.5 \leq f33/f34 \leq 1.5 \quad (6)''$$

According to a preferred aspect of the present embodiment, it is preferable that the following conditional expression (7) be satisfied. The conditional expression (7) defines an appropriate ratio of f31 to f1. It is preferable that, in particular, the refractive power of the 3-1st group G3-1 positioned nearest to the object in the third group G3 be configured appropriately in order to correct the remaining aberrations of the first group G1.

$$-30 \leq f31/f1 \leq -3 \quad (7)$$

where f31 denotes a focal length of the 3-1st group G3-1, and
f1 denotes a focal length of the first group G1.

When the conditional expression (7) takes a value larger than the upper limit value thereof, the refractive power of the first group G1 becomes excessively small and thus the back focus cannot be secured, or, the refractive power of the 3-1st group G3-1 becomes excessively large and thus spherical aberration and longitudinal chromatic aberration are overcorrected.

When the conditional expression (7) takes a value smaller than the lower limit value thereof, the refractive power of the first group G1 becomes excessively large and thus aberrations generally deteriorate, or, the refractive power of the 3-1st group G3-1 becomes excessively small and thus spherical aberration and longitudinal chromatic aberration are undercorrected.

It is more preferable that the following conditional expression (7)' be satisfied:

$$-25 \leq f31/f1 \leq -3.5 \quad (7)'$$

It is further preferable that the following conditional expression (7)" be satisfied:

$$-20 \leq f31/f1 \leq -4 \quad (7)''$$

According to a preferred aspect of the present embodiment, it is preferable that the following conditional expression (8) be satisfied. The conditional expression (8) defines an appropriate ratio of f334 to f1. In the first group G1 positioned nearest to the object and the 3-3rd group G3-3 and the 3-4th group G3-4 positioned nearest to the image, the ray height becomes high at the peripheral of each screen and thus coma and astigmatism are generated. For this reason, it is preferable that these groups have balanced refractive powers.

$$-4 \leq f334/f1 \leq -1 \quad (8)$$

where f334 denotes a combined focal length of the 3-3rd group G3-3 and the 3-4th group G3-4, and
f1 denotes a focal length of the first group G1.

When the conditional expression (8) takes a value larger than the upper limit value thereof, the refractive powers of the 3-3rd group G3-3 and the 3-4th group G3-4 become excessively large and thus coma and astigmatism are overcorrected, or, the refractive power of the first group G1 becomes excessively small and thus the total length becomes long.

When the conditional expression (8) takes a value smaller than the lower limit value thereof, the refractive powers of the 3-3rd group G3-3 and the 3-4th group G3-4 become excessively small and thus coma and astigmatism are undercorrected, or, the refractive power of the first group G1 becomes excessively large and thus aberrations generally deteriorate.

It is more preferable that the following conditional expression (8)' be satisfied:

$$-3.7 \leq f334/f1 \leq -1.2 \quad (8)'$$

It is further preferable that the following conditional expression (8)" be satisfied:

$$-3.5 \leq f334/f1 \leq -1.5 \quad (8)''$$

According to a preferred aspect of the present embodiment, it is preferable that the following conditional expression (9) be satisfied. The conditional expression (9) defines an appropriate ratio of f323 to f3. The negative refractive power of the 3-2nd group G3-2 and the positive refractive power of the 3-3rd group G3-3 are required to be balanced to secure a positive refractive power related to imaging and to correct aberrations.

$$1 \leq f323/f3 \leq 5 \quad (9)$$

where f323 denotes a combined focal length of the 3-2nd group G3-2 and the 3-3rd group G3-3, and f3 denotes the focal length of the third group G3.

When the conditional expression (9) takes a value larger than the upper limit value thereof, the positive refractive power of the 3-3rd group G3-3 becomes excessively small and thus the total length becomes long, or, the negative refractive power of the 3-2nd group G3-2 becomes excessively large and thus spherical aberration and coma are overcorrected.

When the conditional expression (9) takes a value smaller than the lower limit value thereof, the positive refractive power of the 3-3rd group G3-3 becomes excessively large and thus coma and astigmatism deteriorate, or, the negative refractive power of the 3-4th group G3-4 becomes excessively small and thus spherical aberration and coma are undercorrected.

It is more preferable that the following conditional expression (9)' be satisfied:

$$1.5 \leq f323/f3 \leq 3.5 \quad (9)'$$

It is further preferable that the following conditional expression (9)" be satisfied:

$$2 \leq f323/f3 \leq 4 \quad (9)''$$

The examples will be explained hereinafter.

Example 1

FIG. 2A is a sectional view of a lens of an objective optical system for an endoscope in the normal observation state according to Example 1. FIG. 2B is a sectional view of the lens of the objective optical system for an endoscope in the close observation state according to Example 1.

The objective optical system for an endoscope according to Example 1 includes, in order from the object side: a first group G1 having a negative refractive power; a second group G2 having a positive refractive power; and a third group G3 having a positive refractive power. The first group G1 and the third group G3 are fixed and the second group G2 is movable. The second group G2 moves toward an image side in the close observation state.

The first lens group G1 having a negative refractive power includes, in order from the object side: a plano-concave negative first lens L1 with a flat surface directed to the object side; an infrared-cut filter F1; a biconcave negative second lens L2; and a biconvex positive third lens L3. The negative second lens L2 and the positive third lens L3 are cemented to form a cemented lens CL1 having a combined focal length of a negative refractive power.

The second group G2 having a positive refractive power includes a positive fourth meniscus lens L4 with a convex surface directed to the object side. The positive fourth meniscus lens L4 moves toward the image side when performing focusing from the normal observation state to the close observation state.

The third lens group G3 having a positive refractive power includes, in order from the object side: a biconvex positive fifth lens L5; a negative sixth meniscus lens L6 with a convex surface directed to the image; an aperture stop S; a negative seventh meniscus lens L7 with a convex surface directed to the object side; a plano-convex positive eighth lens L8 with a flat surface directed to the object side; a negative ninth meniscus lens L9 with a convex surface directed to the image; and a biconvex positive tenth lens L10. The positive fifth lens L5 and the negative sixth meniscus lens L6 are cemented to form a cemented lens CL2 having a combined focal length of a positive refractive power, and the positive eighth lens L8 and the negative ninth meniscus lens L9 are cemented to form a cemented lens CL3 having a combined focal length of a positive refractive power. In addition, filters F2, F3 and a prism PR are disposed on the image side of the objective optical system. The image side surface of the prism PR is an image pickup surface I.

Figure 3A:
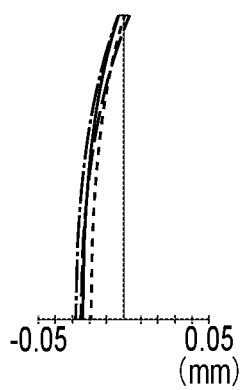
FIG. 3A illustrates spherical aberration (SA) in the normal observation state.
Figure 3B:
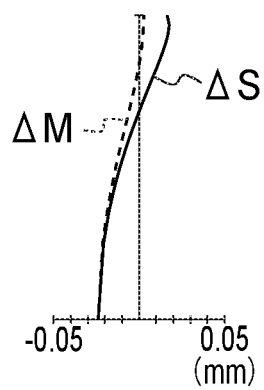
FIG. 3B illustrates astigmatism (AS) in the normal observation state.
Figure 3C:
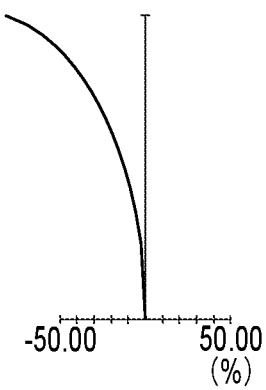
FIG. 3C illustrates distortion (DT) in the normal observation state.
Figure 3D:
FIG. 3D illustrates a chromatic aberration of magnification (CC) in the normal observation state, for the objective optical system for an endoscope according to Example 1.

FIG. 3A illustrates spherical aberration (SA) in the normal observation state, FIG. 3B illustrates astigmatism (AS) in the normal observation state, FIG. 3C illustrates distortion (DT) in the normal observation state, and FIG. 3D illustrates a chromatic aberration of magnification (CC) in the normal observation state, for the objective optical system for an endoscope according to Example 1.

Figure 3E:
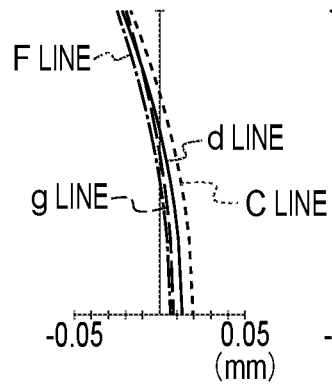
FIG. 3E illustrates spherical aberration (SA) in the close observation state.
Figure 3F:
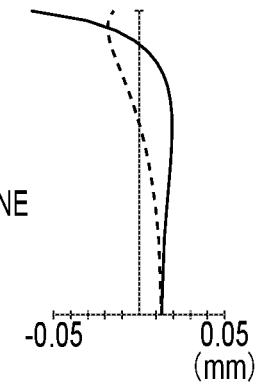
FIG. 3F illustrates astigmatism (AS) in the close observation state.
Figure 3G:
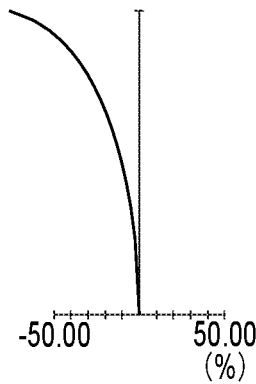
FIG. 3G illustrates distortion (DT) in the close observation state.
Figure 3H:
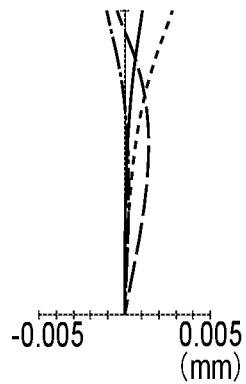
FIG. 3H illustrates a chromatic aberration of magnification (CC) in the close observation state, for the objective optical system for an endoscope according to Example 1.

FIG. 3E illustrates spherical aberration (SA) in the close observation state, FIG. 3F illustrates astigmatism (AS) in the close observation state, FIG. 3G illustrates distortion (DT) in the close observation state, and FIG. 3H illustrates a chromatic aberration of magnification (CC) in the close observation state, for the objective optical system for an endoscope according to Example 1.

Example 2

FIG. 4A is a sectional view of a lens of an objective optical system for an endoscope in the normal observation state according to Example 2. FIG. 4B is a sectional view of the lens of the objective optical system for an endoscope in the close observation state according to Example 2.

The objective optical system for an endoscope according to Example 2 includes, in order from the object side: a first group G1 having a negative refractive power; a second group G2 having a positive refractive power; and a third group G3 having a positive refractive power. The first group G1 and the third group G3 are fixed and the second group G2 is movable. The second group G2 moves toward an image side in the close observation state.

The first lens group G1 having a negative refractive power includes, in order from the object side: a negative first meniscus lens L1 with a convex surface directed to the object side; an infrared-cut filter F1; a biconcave negative second lens L2; and a biconvex positive third lens L3. The negative second lens L2 and the positive third lens L3 are cemented to form a cemented lens CL1 having a combined focal length of a negative refractive power.

The second group G2 having a positive refractive power includes a positive fourth meniscus lens L4 with a convex surface directed to the object side. The positive fourth meniscus lens L4 moves toward the image side when performing focusing from the normal observation state to the close observation state.

The third lens group G3 having a positive refractive power includes, in order from the object side: a biconvex positive fifth lens L5; a negative sixth meniscus lens L6 with a convex surface directed to the image; an aperture stop S; a negative seventh meniscus lens L7 with a convex surface directed to the object side; a biconvex positive eighth lens L8; a negative ninth meniscus lens L9 with a convex surface directed to the image; and a biconvex positive tenth lens L10. The positive fifth lens L5 and the negative sixth meniscus lens L6 are cemented to form a cemented lens CL2 having a combined focal length of a positive refractive power, and the positive eighth lens L8 and the negative ninth meniscus lens L9 are cemented to form a cemented lens CL3 having a combined focal length of a positive refractive power. In addition, filters F2, F3 and a prism PR are disposed on the image side of the objective optical system. The image side surface of the prism PR is an image pickup surface I.

FIG. 5A illustrates spherical aberration (SA) in the normal observation state, FIG. 5B illustrates astigmatism (AS) in the normal observation state, FIG. 5C illustrates distortion (DT) in the normal observation state, and FIG. 5D illustrates a chromatic aberration of magnification (CC) in the normal observation state, for the objective optical system for an endoscope according to Example 2.

FIG. 5E illustrates spherical aberration (SA) in the close observation state, FIG. 5F illustrates astigmatism (AS) in the close observation state, FIG. 5G illustrates distortion (DT) in the close observation state, and FIG. 5H illustrates a chromatic aberration of magnification (CC) in the close observation state, for the objective optical system for an endoscope according to Example 2.

Example 3

FIG. 6A is a sectional view of a lens of an objective optical system for an endoscope in the normal observation state according to Example 3. FIG. 6B is a sectional view of the lens of the objective optical system for an endoscope in the close observation state according to Example 3.

The objective optical system for an endoscope according to Example 3 includes, in order from an object side: a first group G1 having a negative refractive power; a second group G2 having a positive refractive power; and a third group G3 having a positive refractive power. The first group G1 and the third group G3 are fixed and the second group G2 is movable. The second group G2 moves toward an image side in the close observation state.

The first lens group G1 having a negative refractive power includes, in order from the object side: a plano-concave negative first lens L1 with a flat surface directed to the object side; an infrared-cut filter F1; a biconcave negative second lens L2; and a biconvex positive third lens L3. The negative second lens L2 and the positive third lens L3 are cemented to form a cemented lens CL1 having a combined focal length of a negative refractive power.

The second group G2 having a positive refractive power includes a positive fourth meniscus lens L4 with a convex surface directed to the object side. The positive fourth meniscus lens L4 moves toward the image side when performing focusing from the normal observation state to the close observation state.

The third lens group G3 having a positive refractive power includes, in order from the object side: a biconvex positive fifth lens L5; a negative sixth meniscus lens L6 with a convex surface directed to the image; an aperture stop S; a biconcave negative seventh lens L7; a plano-convex positive eighth lens L8; a negative ninth meniscus lens L9 with a convex surface directed to the image; and a biconvex positive tenth lens L10. The positive fifth lens L5 and the negative sixth meniscus lens L6 are cemented to form a cemented lens CL2 having a combined focal length of a positive refractive power, and the positive eighth lens L8 and the negative ninth meniscus lens L9 are cemented to form a cemented lens CL3 having a combined focal length of a positive refractive power. In addition, filters F2, F3 and a prism PR are disposed on the image side of the objective optical system. The image side surface of the prism PR is an image pickup surface I.

FIG. 7A illustrates spherical aberration (SA) in the normal observation state, FIG. 7B illustrates astigmatism (AS) in the normal observation state, FIG. 7C illustrates distortion (DT) in the normal observation state, and FIG. 7D illustrates a chromatic aberration of magnification (CC) in the normal observation state, for the objective optical system for an endoscope according to Example 3.

FIG. 7E illustrates spherical aberration (SA) in the close observation state, FIG. 7F illustrates astigmatism (AS) in the close observation state, FIG. 7G illustrates distortion (DT) in the close observation state, and FIG. 7H illustrates a chromatic aberration of magnification (CC) in the close observation state, for the objective optical system for an endoscope according to Example 3.

Example 4

FIG. 8A is a sectional view of a lens of an objective optical system for an endoscope in the normal observation state according to Example 4. FIG. 8B is a sectional view of the lens of the objective optical system for an endoscope in the close observation state according to Example 4.

The objective optical system for an endoscope according to Example 4 includes, in order from the object side: a first group G1 having a negative refractive power; a second group G2 having a positive refractive power; and a third group G3 having a positive refractive power. The first group G1 and the third group G3 are fixed and the second group G2 is movable. The second group G2 moves toward an image side in the close observation state.

The first lens group G1 having a negative refractive power includes, in order from the object side: a plano-concave negative first lens L1 with a flat surface directed to the object side; an infrared-cut filter F1; a biconcave negative second lens L2; and a biconvex positive third lens L3. The negative second lens L2 and the positive third lens L3 are cemented to form a cemented lens CL1 having a combined focal length of a negative refractive power.

The second group G2 having a positive refractive power includes a positive fourth meniscus lens L4 with a convex surface directed to the object side. The positive fourth meniscus lens L4 moves toward the image side when performing focusing from the normal observation state to the close observation state.

The third lens group G3 having a positive refractive power includes, in order from the object side: a biconvex positive fifth lens L5; a negative sixth meniscus lens L6 with a convex surface directed to the image; an aperture stop S; a biconcave negative seventh lens L7; a plano-convex positive eighth lens L8 with a flat surface directed to the object side; a negative ninth meniscus lens L9 with a convex surface directed to the image; and a biconvex positive tenth lens L10. The positive fifth lens L5 and the negative sixth meniscus lens L6 are cemented to form a cemented lens CL2 having a combined focal length of a positive refractive power. The positive eighth lens L8 and the negative ninth meniscus lens L9 are cemented to form a cemented lens CL3 having a combined focal length of a positive refractive power. In addition, filters F2, F3 and a prism PR are disposed on the image side of the objective optical system. The image side surface of the prism PR is an image pickup surface I.

FIG. 9A illustrates spherical aberration (SA) in the normal observation state, FIG. 9B illustrates astigmatism (AS) in the normal observation state, FIG. 9C illustrates distortion (DT) in the normal observation state, and FIG. 9D illustrates a chromatic aberration of magnification (CC) in the normal observation state, for the objective optical system for an endoscope according to Example 4.

FIG. 9E illustrates spherical aberration (SA) in the close observation state, FIG. 9F illustrates astigmatism (AS) in the close observation state, FIG. 9G illustrates distortion (DT) in the close observation state, and FIG. 9H illustrates a chromatic aberration of magnification (CC) in the close observation state, for the objective optical system for an endoscope according to Example 4.

Examples of numerical values will be listed hereinafter. r1, r2, . . . denote a radius of curvature of each lens surface. d1, d2, . . . denote a thickness and surface distance of each lens. n1, n2, . . . denote a refractive index at the e-line for each lens. ν1, ν2, . . . denote Abbe's number at the d-line for each lens. Stop is an aperture stop.

Example 1

Unit mm

Surface data

| Surface no. | r | d | nd | νd |
|---|---|---|---|---|
| 1 | ∞ | 0.3067 | 1.88815 | 40.76 |
| 2 | 1.1919 | 0.5784 | | |
| 3 | ∞ | 0.2629 | 1.523 | 65.12 |
| 4 | ∞ | 0.2717 | | |
| 5 | −2.1185 | 0.2805 | 1.88815 | 40.76 |
| 6 | 3.1475 | 0.7733 | 1.85504 | 23.78 |
| 7 | −2.9912 | Variable | 0.3327~1.0978 | |
| 8 | 1.5011 | 0.6092 | 1.48915 | 70.23 |
| 9 | 1.8088 | Variable | 1.2561~0.4911 | |
| 10 | 3.2167 | 0.79 | 1.55098 | 45.79 |
| 11 | −1.2143 | 0.2805 | 1.83945 | 42.73 |
| 12 | −4.6985 | 0.0088 | | |
| 13(Stop) | ∞ | 0.0263 | | |
| 14 | 4.0633 | 0.2805 | 1.59667 | 35.31 |
| 15 | 2.949 | 0.1552 | | |
| 16 | ∞ | 0.6995 | 1.48915 | 70.23 |
| 17 | −1.4477 | 0.2805 | 1.97189 | 17.47 |
| 18 | −2.0892 | 0.0857 | | |
| 19 | 9.0328 | 0.4807 | 1.75844 | 52.32 |
| 20 | −7.0245 | 0.3194 | | |
| 21 | ∞ | 0.1753 | 1.51825 | 64.14 |
| 22 | ∞ | 0.1516 | 1.51825 | 64.14 |
| 23 | ∞ | 0.1928 | | |
| 24 | ∞ | 5.1902 | 1.64129 | 55.38 |
| 25 | ∞ | 0 | | |
| 26(Image plane) | ∞ | 0 | | |

Various data

| | Normal observation state | Close observation state |
|---|---|---|
| Object distance | 20 | 2.35 |
| Fno | 4.45 | 4.48 |
| ω | 80.1° | 79.8° |
| IH | 1.0 | |
| d7 | 0.3327 | 1.0978 |
| d9 | 1.2561 | 0.4911 |

Example 2

Unit mm

Surface data

| Surface no. | r | d | nd | νd |
|---|---|---|---|---|
| 1 | 15.4934 | 0.3067 | 1.88815 | 40.7 |
| 2 | 1.0334 | 0.6223 | | |
| 3 | ∞ | 0.2629 | 1.523 | 65.12 |
| 4 | ∞ | 0.2279 | | |
| 5 | −2.1616 | 0.2805 | 1.88815 | 40.76 |
| 6 | 1.6293 | 0.7353 | 1.85504 | 23.78 |
| 7 | −4.3089 | Variable | 0.2743~0.6204 | |
| 8 | 1.2585 | 0.6138 | 1.48915 | 70.23 |
| 9 | 1.7264 | Variable | 0.8169~0.4708 | |
| 10 | 2.6012 | 0.75 | 1.55098 | 45.79 |
| 11 | −0.923 | 0.2805 | 1.83945 | 42.73 |
| 12 | −4.488 | 0.0088 | | |
| 13(Stop) | ∞ | 0.0263 | | |
| 14 | 2.4949 | 0.2805 | 1.59667 | 35.31 |
| 15 | 2.1237 | 0.1501 | | |
| 16 | 13.2768 | 0.9006 | 1.48915 | 70.23 |
| 17 | −1.3281 | 0.2805 | 1.97189 | 17.47 |
| 18 | −1.9322 | 0.0805 | | |
| 19 | 17.3989 | 0.4762 | 1.75844 | 52.32 |
| 20 | −5.1127 | 0.2854 | | |
| 21 | ∞ | 0.1753 | 1.51825 | 64.14 |
| 22 | ∞ | 0.1516 | 1.51825 | 64.14 |
| 23 | ∞ | 0.1928 | | |
| 24 | ∞ | 5.1902 | 1.64129 | 55.38 |
| 25 | ∞ | 0 | | |
| 26(Image plane) | ∞ | 0 | | |

Various data

| | Normal observation state | Close observation state |
|---|---|---|
| Object distance | 12.5 | 2.5 |
| Fno | 4.27 | 4.27 |
| ω | 80.1° | 80.0° |
| IH | 1.0 | |
| d7 | 0.2743 | 0.6204 |
| d9 | 0.8169 | 0.4708 |

Example 3

Unit mm

Surface data

| Surface no. | r | d | nd | νd |
|---|---|---|---|---|
| 1 | ∞ | 0.2453 | 1.88815 | 40.76 |
| 2 | 1.1884 | 0.5341 | | |
| 3 | ∞ | 0.2629 | 1.523 | 65.12 |
| 4 | ∞ | 0.2717 | | |
| 5 | −2.5043 | 0.2805 | 1.88815 | 40.76 |
| 6 | 1.5899 | 0.7325 | 1.85504 | 23.78 |
| 7 | −3.5377 | Variable | 0.1846~0.8664 | |

-continued

| Unit mm | | | | |
|---|---|---|---|---|
| 8 | 1.3944 | 0.6181 | 1.48915 | 70.23 |
| 9 | 1.8293 | Variable | 1.0867~0.3905 | |
| 10 | 7.7068 | 0.8528 | 1.55098 | 45.79 |
| 11 | −0.8775 | 0.3067 | 2.01169 | 28.27 |
| 12 | −1.6289 | 0.0213 | | |
| 13(Stop) | ∞ | 0.018 | | |
| 14 | −19.4973 | 0.2805 | 1.59667 | 35.31 |
| 15 | 6.9441 | 0.1011 | | |
| 16 | ∞ | 0.9144 | 1.48915 | 70.23 |
| 17 | −1.7532 | 0.2805 | 1.97189 | 17.47 |
| 18 | −2.1584 | 0.0779 | | |
| 19 | 23.2447 | 0.4121 | 1.75844 | 52.32 |
| 20 | −8.1625 | 0.3194 | | |
| 21 | ∞ | 0.1753 | 1.51825 | 64.14 |
| 22 | ∞ | 0.1516 | 1.51825 | 64.14 |
| 23 | ∞ | 0.1928 | | |
| 24 | ∞ | 5.1902 | 1.64129 | 55.38 |
| 25 | ∞ | 0 | | |
| 26(Image plane) | ∞ | 0 | | |

| Various data | | |
|---|---|---|
| | Normal observation state | Close observation state |
| Object distance | 20 | 2.35 |
| Fno | 4.52 | 4.52 |
| ω | 80.2° | 80.1° |
| IH | 1.0 | |
| d7 | 0.1846 | 0.8664 |
| d9 | 1.0867 | 0.3905 |

Example 4

| Unit mm | | | | |
|---|---|---|---|---|
| Surface data | | | | |
| Surface no. | r | d | nd | vd |
| 1 | ∞ | 0.3067 | 1.88815 | 40.76 |
| 2 | 1.1773 | 0.5418 | | |
| 3 | ∞ | 0.2629 | 1.523 | 65.12 |
| 4 | ∞ | 0.2717 | | |
| 5 | −2.2401 | 0.2805 | 1.88815 | 40.76 |
| 6 | 2.3995 | 0.7312 | 1.85504 | 23.78 |
| 7 | −3.2507 | Variable | 0.1835~0.8572 | |
| 8 | 1.3965 | 0.6212 | 1.48915 | 70.23 |
| 9 | 1.811 | Variable | 1.0822~0.3932 | |
| 10 | 5.2485 | 0.8963 | 1.55098 | 45.79 |
| 11 | −0.8874 | 0.2805 | 1.83945 | 42.73 |
| 12 | −2.1995 | 0.0166 | | |
| 13(Stop) | ∞ | 0.0667 | | |
| 14 | −28.6586 | 0.2805 | 1.59667 | 35.31 |
| 15 | 7.5342 | 0.0679 | | |
| 16 | ∞ | 0.8488 | 1.48915 | 70.23 |
| 17 | −1.2219 | 0.2805 | 1.97189 | 17.47 |
| 18 | −1.6691 | 0.0689 | | |
| 19 | 21.8432 | 0.3939 | 1.75844 | 52.32 |
| 20 | −8.8864 | 0.3194 | | |
| 21 | ∞ | 0.1753 | 1.51825 | 64.14 |
| 22 | ∞ | 0.1516 | 1.51825 | 64.14 |
| 23 | ∞ | 0.1928 | | |
| 24 | ∞ | 5.1902 | 1.64129 | 55.38 |
| 25 | ∞ | 0 | | |
| 26(Image plane) | ∞ | 0 | | |

-continued

| Unit mm | | |
|---|---|---|
| Various data | | |
| | Normal observation state | Close observation state |
| Object distance | 20 | 2.35 |
| Fno | 4.37 | 4.38 |
| ω | 79.9° | 80.1° |
| IH | 1.0 | |
| d7 | 0.1835 | 0.8572 |
| d9 | 1.0822 | 0.3932 |

Values of the conditional expressions of each examples are shown below.

(1) Bk/f3
(2) f31/f3
(3) f33/f3
(4) f32/f334
(5) f31/f33
(6) f33/f34
(7) f31/f1
(8) f334/f1
(9) f323/f3

| Conditional Expression | | | | |
|---|---|---|---|---|
| | Example1 | Example2 | Example3 | Example4 |
| (1) | 2.11 | 2.21 | 2.24 | 2.21 |
| (2) | 2.95 | 3.64 | 1.81 | 2.16 |
| (3) | 2.28 | 1.88 | 1.93 | 1.67 |
| (4) | −6.87 | −12.66 | −2.70 | −3.39 |
| (5) | 1.30 | 1.94 | 0.94 | 1.30 |
| (6) | 1.23 | 0.97 | 0.65 | 0.54 |
| (7) | −6.39 | −10.37 | −3.91 | −4.74 |
| (8) | −2.20 | −2.76 | −2.53 | −2.37 |
| (9) | 3.25 | 2.25 | 3.70 | 2.56 |

The aforementioned objective optical system for an endoscope may satisfy the plurality of configurations at once. Such a design is preferable to obtain a favorable objective optical system for an endoscope. The favorable configurations can be combined arbitrarily. It is possible to limit only the upper limit value or the lower limit value of the further limited numerical range for each conditional expression.

Various embodiments of the present disclosure have been explained, but the present disclosure is not limited to only these embodiments. In addition, any embodiment implemented by appropriately combining the configurations of these embodiments without departing from the gist of the present disclosure is within a scope of the present disclosure.

As described above, the present disclosure is suitable for a high-performance objective optical system, an image pickup apparatus, an endoscope, and an endoscope system that are capable of securing a back focus and supporting high resolution.

According to the present disclosure, it is possible to provide a high-performance objective optical system, an image pickup apparatus, an endoscope, and an endoscope system that are capable of securing a back focus that allows a prism to be disposed therein and supporting high resolution.

What is claimed is:

1. An objective optical system comprising, in order from an object side:
   a first group having a negative refractive power;
   a second group having a positive refractive power; and
   a third group having a positive refractive power,
   wherein:
   the first group and the third group are fixed and the second group is movable,
   the first group includes at least two lenses having a negative refractive power,
   the third group includes, in order from the object side, a 3-1st group having a positive refractive power, a 3-2nd group having a negative refractive power, a 3-3rd group having a positive refractive power, and a 3-4th group having a positive refractive power,
   the 3-1st group includes a cemented lens, and
   the following conditional expressions (1)''' and (2) are satisfied:

$$1.5 \leq Bk/f3 \leq 6 \quad (1)'''$$

$$1.2 \leq f31/f3 \leq 5 \quad (2)$$

where
   Bk denotes a distance from a surface of the third group positioned nearest to an image to an image plane along an optical axis,
   f3 denotes a focal length of the third group, and
   f31 denotes a focal length of the 3-1st group.

2. The objective optical system according to claim 1, wherein:
   the 3-3rd group includes a cemented lens, and
   the following conditional expression (3) is satisfied:

$$1 \leq f33/f3 \leq 5 \quad (3)$$

where f33 denotes a focal length of the 3-3rd group.

3. The objective optical system according to claim 1, wherein the following conditional expression (6) is satisfied:

$$0.3 \leq f33/f34 \leq 2.5 \quad (6)$$

where
   f33 denotes a focal length of the 3-3rd group, and
   f34 denotes a focal length of the 3-4th group.

4. The objective optical system according to claim 1, wherein the following conditional expression (8) is satisfied:

$$-4 \leq f334/f1 \leq -1 \quad (8)$$

where
   f334 denotes a combined focal length of the 3-3rd group and the 3-4th group, and
   f1 denotes a focal length of the first group.

5. An image pickup apparatus comprising the objective optical system according to claim 1.

6. An endoscope comprising the objective optical system according to claim 1.

7. An endoscope system comprising:
   the endoscope according to claim 6; and
   an image processor.

8. An objective optical system comprising, in order from an object side:
   a first group having a negative refractive power;
   a second group having a positive refractive power; and
   a third group having a positive refractive power,
   wherein:
   the first group and the third group are fixed and the second group is movable,
   the first group includes at least two lenses having a negative refractive power,
   the third group includes, in order from the object side, a 3-1st group having a positive refractive power, a 3-2nd group having a negative refractive power, a 3-3rd group having a positive refractive power, and a 3-4th group having a positive refractive power, and
   the following conditional expressions (1)''' and (4) are satisfied:

$$1.5 \leq Bk/f3 \leq 6 \quad (1)'''$$

$$-30 \leq f32/f334 \leq -1.5 \quad (4)$$

where
   Bk denotes a distance from a surface of the third group positioned nearest to an image to an image plane along an optical axis,
   f3 denotes a focal length of the third group,
   f334 denotes a combined focal length of the 3-3rd group and the 3-4th group, and
   f32 denotes a focal length of the 3-2nd group.

9. An objective optical system comprising, in order from an object side:
   a first group having a negative refractive power;
   a second group having a positive refractive power; and
   a third group having a positive refractive power,
   wherein:
   the first group and the third group are fixed and the second group is movable,
   the first group includes at least two lenses having a negative refractive power,
   the third group includes, in order from the object side, a 3-1st group having a positive refractive power, a 3-2nd group having a negative refractive power, a 3-3rd group having a positive refractive power, and a 3-4th group having a positive refractive power, and
   the following conditional expressions (1)''' and (5) are satisfied:

$$1.5 \leq Bk/f3 \leq 6 \quad (1)'''$$

$$0.5 \leq f31/f33 \leq 5 \quad (5)$$

where
   Bk denotes a distance from a surface of the third group positioned nearest to an image to an image plane along an optical axis,
   f3 denotes a focal length of the third group,
   f31 denotes a focal length of the 3-1st group, and
   f33 denotes a focal length of the 3-3rd group.

10. An objective optical system comprising, in order from an object side:
    a first group having a negative refractive power;
    a second group having a positive refractive power; and
    a third group having a positive refractive power,
    wherein:
    the first group and the third group are fixed and the second group is movable,
    the first group includes at least two lenses having a negative refractive power,
    the third group includes, in order from the object side, a 3-1st group having a positive refractive power, a 3-2nd group having a negative refractive power, a 3-3rd group having a positive refractive power, and a 3-4th group having a positive refractive power, and
    the following conditional expressions (1)''' and (7) are satisfied:

$$1.5 \leq Bk/f3 \leq 6 \quad (1)'''$$

$$-30 \leq f31/f1 \leq -3 \quad (7)$$

where
Bk denotes a distance from a surface of the third group positioned nearest to an image to an image plane along an optical axis,
f3 denotes a focal length of the third group,
f31 denotes a focal length of the 3-1st group, and
f1 denotes a focal length of the first group.

11. An objective optical system comprising, in order from an object side:
a first group having a negative refractive power;
a second group having a positive refractive power; and
a third group having a positive refractive power,
wherein:
the first group and the third group are fixed and the second group is movable,
the first group includes at least two lenses having a negative refractive power,
the third group includes, in order from the object side, a 3-1st group having a positive refractive power, a 3-2nd group having a negative refractive power, a 3-3rd group having a positive refractive power, and a 3-4th group having a positive refractive power, and
the following conditional expression expressions (1)''' and (9) are satisfied:

$$1.5 \leq Bk/f3 \leq 6 \quad (1)'''$$

$$1 \leq f323/f3 \leq 5 \quad (9)$$

where
Bk denotes a distance from a surface of the third group positioned nearest to an image to an image plane along an optical axis,
f3 denotes a focal length of the third group, and
f323 denotes a combined focal length of the 3-2nd group and the 3-3rd group.

* * * * *